United States Patent
Minagawa

(10) Patent No.: US 9,850,445 B2
(45) Date of Patent: Dec. 26, 2017

(54) SLIDING ELASTIC BODY

(71) Applicant: SUMITOMO RUBBER INDUSTRIES, LTD., Kobe-shi, Hyogo (JP)

(72) Inventor: Yasuhisa Minagawa, Kobe (JP)

(73) Assignee: SUMITOMO RUBBER INDUSTRIES, LTD., Kobe-Shi, Hyogo (JP)

( * ) Notice: Subject to any disclaimer, the term of this patent is extended or adjusted under 35 U.S.C. 154(b) by 0 days.

(21) Appl. No.: 14/654,756

(22) PCT Filed: Jan. 6, 2014

(86) PCT No.: PCT/JP2014/050007
§ 371 (c)(1),
(2) Date: Jun. 22, 2015

(87) PCT Pub. No.: WO2014/106951
PCT Pub. Date: Jul. 10, 2014

(65) Prior Publication Data
US 2015/0344803 A1    Dec. 3, 2015

(30) Foreign Application Priority Data

Jan. 7, 2013    (JP) .................................. 2013-000644

(51) Int. Cl.
*C10M 107/38*    (2006.01)
*A61M 5/315*    (2006.01)
(Continued)

(52) U.S. Cl.
CPC ......... *C10M 107/38* (2013.01); *A61L 29/041* (2013.01); *A61M 5/315* (2013.01);
(Continued)

(58) Field of Classification Search
CPC ...... C10M 107/38; C10M 2213/06062; A61M 5/315; A61M 5/31513; B60C 11/00;
(Continued)

(56) References Cited

U.S. PATENT DOCUMENTS

2004/0103966 A1    6/2004  Boes et al.
2005/0137533 A1    6/2005  Sudo et al.
(Continued)

FOREIGN PATENT DOCUMENTS

EP    1674121 A1    6/2006
JP    5-208454 A    8/1993
(Continued)

OTHER PUBLICATIONS

International Search Report, issued in PCT/JP2014/050007, dated Mar. 25, 2014.

*Primary Examiner* — Cephia D Toomer
(74) *Attorney, Agent, or Firm* — Birch, Stewart, Kolasch & Birch, LLP

(57) ABSTRACT

Provided are a sliding elastic body capable of imparting excellent sliding properties and resistance to protein adsorption and, at the same time, maintaining sealing properties; and a syringe gasket, a catheter, and a tire which include the sliding elastic body. The present invention relates to a sliding elastic body including an elastic body whose surface is fully or partially laminated with a fluororesin film, the laminated elastic body being treated with a fluorinated oil.

4 Claims, 2 Drawing Sheets

(51) Int. Cl.
| | | |
|---|---|---|
| B60C 11/00 | (2006.01) | |
| B60C 1/00 | (2006.01) | |
| A61L 29/04 | (2006.01) | |
| B32B 27/30 | (2006.01) | |
| B60C 11/13 | (2006.01) | |
| B32B 27/32 | (2006.01) | |
| B32B 1/00 | (2006.01) | |
| B32B 3/04 | (2006.01) | |
| B32B 3/28 | (2006.01) | |
| B60C 13/04 | (2006.01) | |
| B32B 25/08 | (2006.01) | |
| B32B 25/18 | (2006.01) | |

(52) U.S. Cl.
CPC ........... *A61M 5/31513* (2013.01); *B32B 1/00* (2013.01); *B32B 3/04* (2013.01); *B32B 3/28* (2013.01); *B32B 27/304* (2013.01); *B32B 27/322* (2013.01); *B60C 1/00* (2013.01); *B60C 1/0016* (2013.01); *B60C 1/0025* (2013.01); *B60C 11/00* (2013.01); *B60C 11/1346* (2013.01); *A61L 2400/10* (2013.01); *B32B 25/08* (2013.01); *B32B 25/18* (2013.01); *B32B 2274/00* (2013.01); *B32B 2307/51* (2013.01); *B32B 2307/746* (2013.01); *B32B 2535/00* (2013.01); *B32B 2581/00* (2013.01); *B60C 2013/045* (2013.01); *C10M 2213/0606* (2013.01); *C10N 2240/22* (2013.01); *C10N 2240/66* (2013.01)

(58) Field of Classification Search
CPC ... B60C 1/00; B60C 1/0016; B60C 2013/045; B60C 11/1346; A61L 29/041; A61L 2400/10; B32B 27/304; B32B 2307/51; B32B 2581/00; B32B 25/08; B32B 25/18; B32B 27/322; B32B 1/00; B32B 3/04; B32B 3/28; B32B 2274/00; B32B 2307/746; B32B 2535/00; C10N 2240/22; C10N 2240/66
See application file for complete search history.

(56) References Cited

U.S. PATENT DOCUMENTS

| | | | |
|---|---|---|---|
| 2006/0069356 A1* | 3/2006 | Witowski | A61M 5/31511 604/222 |
| 2006/0178643 A1 | 8/2006 | Sudo et al. | |
| 2006/0199911 A1* | 9/2006 | Markovich | C08L 23/0815 525/192 |
| 2010/0316421 A1* | 12/2010 | Komuro | G03G 15/2032 399/329 |
| 2014/0031764 A1 | 1/2014 | Abe et al. | |

FOREIGN PATENT DOCUMENTS

| | | |
|---|---|---|
| JP | 8-71143 A | 3/1996 |
| JP | 2003-190285 A | 7/2003 |
| JP | 2004-38075 A | 2/2004 |
| JP | 2004-298220 A | 10/2004 |
| JP | 2005-137771 A | 6/2005 |
| JP | 2005-177005 A | 7/2005 |
| JP | 2006-181027 A | 7/2006 |
| JP | 2006-288652 A | 10/2006 |
| JP | 2010-142573 A | 7/2010 |
| WO | WO 2012/133264 A1 | 10/2012 |

* cited by examiner

SLIDING ELASTIC BODY

TECHNICAL FIELD

The present invention relates to a sliding elastic body, and a syringe gasket, a catheter, and a tire which include the sliding elastic body.

BACKGROUND ART

With the emphasis on sealing properties, elastic bodies, such as rubber, are used in parts that slide while maintaining a seal, such as a gasket which is integrated with a syringe plunger and forms a seal between the plunger and the barrel. Such elastic bodies, however, have a slight problem in their sliding properties (see Patent Literature 1). Therefore, a sliding property improver, such as silicone oil, is applied to the sliding surface, but it is pointed out that such silicone oil can adversely affect recently marketed bio-preparations. On the other hand, gaskets not coated with silicone oil are remarkably poor in sliding properties and therefore do not allow plungers to be smoothly pushed but cause them to pulsate during administration, resulting in problems such as inaccurate injection amounts and infliction of pain on patients.

In order to satisfy the conflicting requirements, sealing properties and sliding properties, a method of coating surfaces with a self-lubricating PTFE film has been proposed (see Patent Literature 2). Although the surfaces coated with a PTFE film achieve sufficient sliding properties, there still exists a need to further enhance sliding properties. Moreover, the PTFE film coating can sufficiently reduce adsorption of proteins contained in bio-preparations, but there remains a need for further reduction in the adsorption.

Furthermore, the use in other applications where sliding properties in the presence of water are required can be considered. Specifically, water can be delivered without a loss by reducing the fluid resistance of the inner surface of a pre-filled syringe or of the inner surface of a pipe or tube for delivering water, or by increasing or greatly reducing the contact angle with water. Also, drainage of water on wet roads and of snow on snowy roads can be improved by reducing the fluid resistance of the groove surfaces of tires, or by increasing or greatly reducing the contact angle with water. This results in enhanced grip performance, and therefore better safety. In addition, less adhesion of wastes and dusts can be expected when the sliding resistance of the sidewall surfaces of tires or the walls of buildings is reduced, or when their contact angle with water is increased.

Further advantageous effects can be expected, including, for example: less pressure loss when water, an aqueous solution, or the like is delivered through a diaphragm such as a diaphragm pump or valve; easy sliding of skis and snowboards by enhancing the sliding properties of the sliding surfaces thereof; better noticeability of road signs and signboards by enhancing the sliding properties thereof to allow snow to slide easily; reduction in water resistance or drag and less adhesion of bacteria on the outer peripheries of ships by reducing the sliding resistance of the outer peripheries, or by increasing the contact angle with water; and reduction in water resistance or drag of swimsuits by improving the sliding properties of the thread surfaces thereof.

CITATION LIST

Patent Literature

Patent Literature 1: JP 2004-298220 A
Patent Literature 2: JP 2010-142573 A

SUMMARY OF INVENTION

Technical Problem

The present invention aims to solve the above problems and provide a sliding elastic body capable of imparting excellent sliding properties and resistance to protein adsorption and, at the same time, maintaining sealing properties; and a syringe gasket, a catheter, and a tire which include the sliding elastic body.

Solution to Problem

The present invention relates to a sliding elastic body, including an elastic body whose surface is fully or partially laminated with a fluororesin film, the laminated elastic body being treated with a fluorinated oil.

The fluororesin film preferably includes polytetrafluoroethylene, modified polytetrafluoroethylene, a tetrafluoroethylene-ethylene copolymer, a tetrafluoroethylene-perfluoro (alkyl vinyl ether) copolymer, a tetrafluoroethylene-hexafluoropropylene copolymer, polyvinylidene fluoride, polychlorotrifluoroethylene, or a chlorotrifluoroethylene-ethylene copolymer.

The fluorinated oil preferably includes a perfluoropolyether.

Moreover, the fluorinated oil preferably includes at least one of compounds represented by the formulas (1) and (2):

$$F-(CF_2CF_2CF_2O)_m-CF_2CF_3 \quad (1)$$

wherein m represents an integer of 1 or more, and

$$F-(CFCF_2O)_n-CF_2CF_3 \quad (2)$$
$$\qquad\quad |$$
$$\qquad\;\; CF_3$$

wherein n represents an integer of 1 or more.

The fluorinated oil preferably has a kinematic viscosity at 40° C. of 40 mm²/s or higher.

The present invention relates to a syringe gasket, including the sliding elastic body.

The present invention relates to a catheter, including the sliding elastic body.

The present invention relates to a tire, including the sliding elastic body.

The present invention also relates to a tire, including a sidewall formed from the sliding elastic body.

Advantageous Effects of Invention

The present invention provides a sliding elastic body including an elastic body whose surface is fully or partially laminated with a fluororesin film, the laminated elastic body being treated with a fluorinated oil. Such a sliding elastic body can impart excellent sliding properties and resistance to protein adsorption and, at the same time, maintain sealing properties. Therefore, a syringe gasket and the like which are excellent in these properties can be provided using such a sliding elastic body.

DESCRIPTION OF EMBODIMENTS

Figure 1:
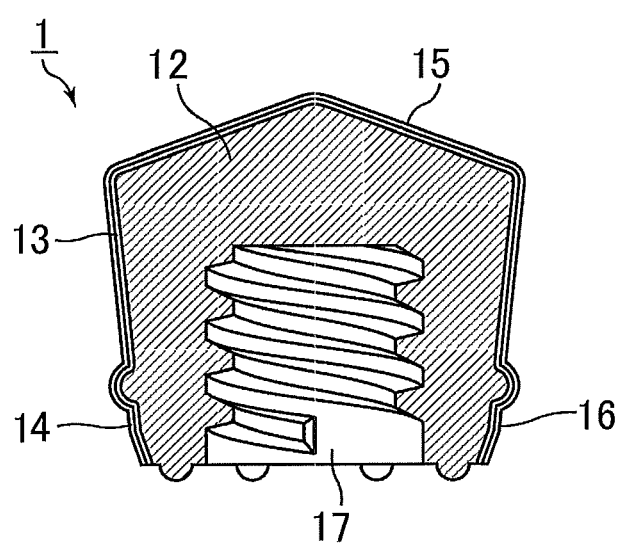
FIG. 1 is a cross-sectional view of an example of a syringe gasket.

The sliding elastic body of the present invention includes an elastic body whose surface is fully or partially laminated with a fluororesin film, and the laminated elastic body is treated with a fluorinated oil. By using such a sliding elastic body, sliding properties and sealing properties can be remarkably improved and, at the same time, protein adsorption to the sliding elastic body can be prevented.

Examples of the elastic body include rubber and thermoplastic elastomers. In particular, it is preferred to use rubber (rubber elastic bodies) because then the effects of the present invention can be well achieved.

Examples of the rubber include diene rubbers such as styrene-butadiene rubber, polybutadiene rubber, polyisoprene rubber, natural rubber, and deproteinized natural rubber; and butyl rubber and halogenated butyl rubber which have a degree of unsaturation of a few percent of isoprene units. The butyl rubber or halogenated butyl rubber, if used, is preferably a rubber crosslinked by triazine because the amount of matter extracted from the rubber vulcanizate is small. In this case, the rubber may contain an acid acceptor, and examples of suitable acid acceptors include hydrotalcite and magnesium carbonate.

If other rubbers are used, sulfur vulcanization is preferably performed. In this case, compounding agents commonly used for sulfur vulcanization may be added, such as vulcanization accelerators, zinc oxide, filler, and silane coupling agents. Suitable examples of the filler include carbon black, silica, clay, talc, and calcium carbonate.

The vulcanization conditions for the rubber may be appropriately adjusted. The vulcanization temperature of the rubber is preferably 150° C. or higher, more preferably 170° C. or higher, and further preferably 175° C. or higher.

Examples of the thermoplastic elastomer include polymer compounds that have rubber elasticity at room temperature owing to aggregates of plastic components (hard segments) serving as crosslinking points (e.g., thermoplastic elastomers (TPE) such as styrene-butadiene-styrene copolymers); and polymer compounds having rubber elasticity, obtained by mixing a thermoplastic component and a rubber component and dynamically crosslinking the mixture by a crosslinking agent (e.g., thermoplastic elastomers (TPV) such as polymer alloys containing a styrenic block copolymer or olefinic resin together with a crosslinked rubber component).

Other suitable examples of the thermoplastic elastomer include nylon, polyester, polyurethane, polypropylene, and dynamically crosslinked thermoplastic elastomers thereof. Preferred among dynamically crosslinked thermoplastic elastomers are those obtained by dynamically crosslinking halogenated butyl rubber in a thermoplastic elastomer. This thermoplastic elastomer is preferably nylon, polyurethane, polypropylene, or SIBS (styrene-isobutylene-styrene block copolymer), for example.

Examples of the fluororesin film includes films of polytetrafluoroethylene (PTFE), tetrafluoroethylene-ethylene copolymers (ETFE), tetrafluoroethylene-perfluoro(alkyl vinyl ether) copolymers (PFA), tetrafluoroethylene-hexafluoropropylene copolymers (FEP), polyvinylidene fluoride (PVDF), polychlorotrifluoroethylene (PCTFE), chlorotrifluoroethylene-ethylene copolymers (ECTFE), and modified resins thereof (e.g. modified PTFE, modified ETFE).

The surface of the elastic body is fully or partially laminated with the fluororesin film. Such lamination can be carried out by known methods. The region to be laminated is not particularly limited, and may be appropriately determined depending on the intended use. For example, a syringe gasket (e.g. pre-filled syringe gasket) generally has a liquid-contacting portion which is in contact with a chemical liquid in the barrel but which does not make contact with the inner wall of the barrel when the gasket slides, a sliding portion (circular sealing portion) which is in contact with the inner wall of the barrel during sliding movement, and an insert hole in which a plunger rod is to be inserted. At least the liquid-contacting portion is preferably laminated with the fluororesin film.

The sliding elastic body of the present invention is obtained by treating the surface of the elastic body coated with a fluororesin film with a fluorinated oil. This treatment enhances sliding properties and durability against repeated sliding movement, and also prevents protein adsorption.

The fluorinated oil is, for example, a substance in the form of liquid or grease at room temperature, resulting from partial or total replacement of the hydrogen atoms in a polyalkyl ether compound by fluorine atoms, and the fluorinated oil may contain a halogen atom such as chlorine or bromine, phosphorus, sulfur, nitrogen or the like.

Examples of the fluorinated oil include fluoropolyethers such as perfluoropolyethers (e.g. perfluoroalkylpolyethers), and hydrofluoroethers, which are commercially available, for example, as the DEMNUM series produced by DAIKIN INDUSTRIES, ltd., or the KRYTOX series produced by Du Pont Kabushiki Kaisha. These may be used alone or two or more of these may be used in combination.

Preferred among the perfluoropolyethers are compounds resulting from total replacement of the hydrogen atoms in polyalkyl ether compounds by fluorine atoms. Particularly preferred are compounds represented by the formula (1) or (2):

$$F-(CF_2CF_2CF_2O)_m-CF_2CF_3 \quad (1)$$

wherein m represents an integer of 1 or more,

$$F-(CFCF_2O)_n-CF_2CF_3 \quad (2)$$
$$\quad\quad\ \ |$$
$$\quad\quad\ \ CF_3$$

wherein n represents an integer of 1 or more.

In the formula (1), m is preferably an integer of 4 to 500, and more preferably 10 to 100. In the formula (2), n is preferably an integer of 4 to 500, and more preferably 7 to 60.

The kinematic viscosity at 40° C. of the fluorinated oil is preferably 10 mm²/s or higher, more preferably 40 mm²/s or higher, and still more preferably 60 mm²/s or higher. A fluorinated oil having a kinematic viscosity of lower than 10 mm$^2$/s may not adsorb on the surface sufficiently to provide the effects such as sliding properties. Also, the upper limit of the kinematic viscosity is preferably 1000 mm$^2$/s or lower, and more preferably 600 mm$^2$/s or lower, because a too highly viscous fluorinated oil does not provide high sliding properties.

The kinematic viscosity (40° C.) can be measured in accordance with JIS K2283.

The surface of the elastic body coated with a fluororesin film may be treated with the fluorinated oil by any method capable of bringing the fluorinated oil into contact with the surface of the coated elastic body, such as, for example, by application, spraying, immersion, or coating. In particular, application or coating is suitable. The surface of the elastic body coated with a fluororesin film may be fully or partially treated with the fluorinated oil, and the treatment may be appropriately determined depending on the intended use. For example, in the case of a syringe gasket, the treatment is preferably carried out on at least the sliding portion of the gasket surface.

FIG. 1 is a cross-sectional view of an example of a syringe gasket. The syringe gasket 1 shown in FIG. 1 is obtained by laminating a fluororesin film 13 to the outer periphery (liquid-contacting portion and sliding portion) of an elastic body 12, which is to be in contact with the inner periphery of a syringe barrel, and coating the film with a fluorinated oil 14. The syringe gasket 1 further includes a liquid-contacting portion 15 to be in contact with a chemical liquid in the barrel, a sliding portion (circular sealing portion) 16 to be in contact with the inner wall of the barrel during sliding movement, and an insert hole 17 in which a plunger rod is to be inserted. With such a configuration, excellent airtightness, sliding properties, and resistance to protein adsorption are imparted. In addition, excellent chemical resistance can be ensured.

Similarly, resistance to protein adsorption and the like can be imparted to a catheter by laminating a fluororesin onto the catheter, and then treating the laminated catheter with a fluorinated oil. The lamination with a fluororesin or the treatment with a fluorinated oil is preferably carried out on at least a portion to be in contact with a biological fluid, such as a catheter surface. It may be carried out on the entire surface.

Furthermore, by laminating a fluororesin to grooves formed on the tread of a tire for use on vehicles such as passenger cars, and treating the laminated grooves with a fluorinated oil, the fluid resistance of the groove surface on wet or snowy roads is reduced, and the contact angle with water is increased. Therefore, the abilities to remove and drain water or snow can be enhanced to improve grip performance.

Figure 2:
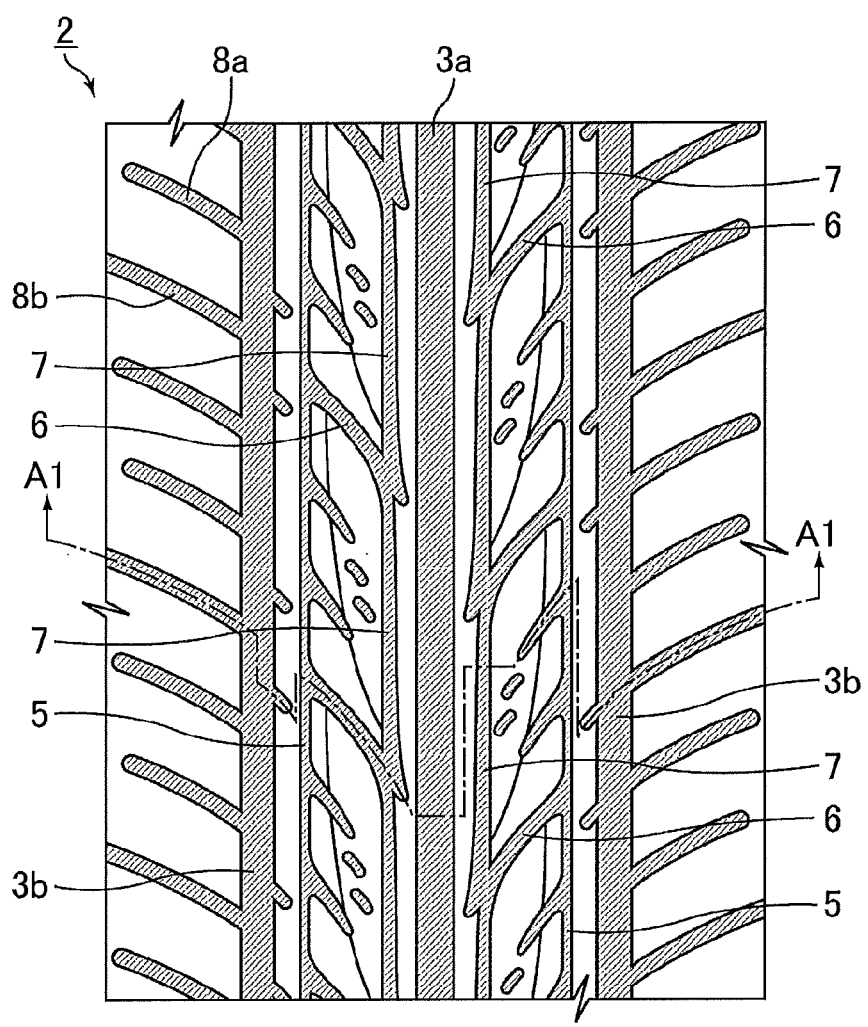
FIG. 2 is a development view of an example of the tread portion of a pneumatic tire (not entirely illustrated).
Figure 3:
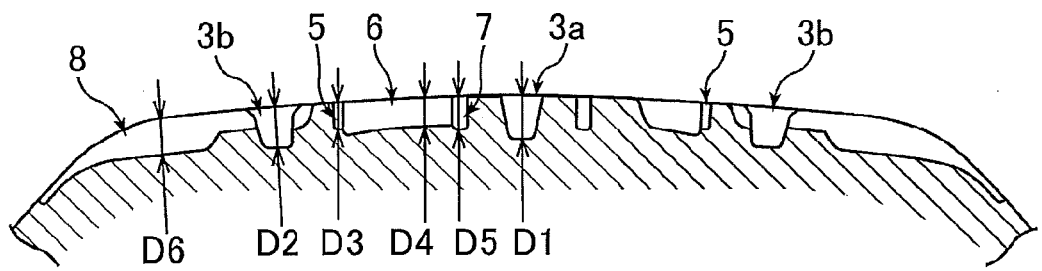
FIG. 3 is an exemplary A1-A1 cross-sectional view of FIG. 2.

FIG. 2 is a development view of an example of the tread portion 2 of a pneumatic tire (not entirely illustrated), and FIG. 3 is an exemplary A1-A1 cross-sectional view of FIG. 2.

In FIGS. 2 and 3, a longitudinal center groove 3a (groove depth D1) and longitudinal shoulder grooves 3b (groove depth D2) are straight grooves linearly extending in the circumferential direction of the tire. Such straight grooves can contribute to low drainage resistance, and high drainage performance during straight running.

The pneumatic tire also has fine grooves 5 (groove depth D3) extending in the tire circumferential direction on the side of the longitudinal shoulder groove 3b; beveled intermediate grooves 6 (groove depth D4) extending with an inclination from the fine groove 5 toward the longitudinal center groove 3a; connecting grooves 7 (groove depth D5) located inward of the fine groove 5 in the axis direction of the tire and connecting the beveled intermediate grooves 6 next to one another in the tire circumferential direction; lateral shoulder grooves 8, 8a, and 8b (groove depth D6) extending from the longitudinal shoulder groove 3b toward the outside of the tire; and the like. These grooves can also contribute to drainage performance. If these grooves are laminated with a fluororesin and treated with a fluorinated oil, then the aforementioned effects can be achieved.

EXAMPLES

The present invention will be specifically described by reference to examples; however, the present invention is not limited thereto.

Example 1

A fluororesin film was laminated to the surface (liquid-contacting portion and sliding portion) of a chlorobutyl rubber (degree of unsaturation: 1-2%) when the rubber was crosslinked by triazine (vulcanized at 180° C. for 10 minutes).

Further, a fluorinated oil 1 (Krytox GPL104 (kinematic viscosity (40° C.): 60 mm$^2$/s) produced by Du Pont Kabushiki Kaisha) was applied to the surface (liquid-contacting portion and sliding portion) to prepare a sliding elastic body.

Example 2

A sliding elastic body was prepared in the same manner as in Example 1, except that a fluorinated oil 2 (Krytox GPL105 (kinematic viscosity (40° C.): 160 mm$^2$/s) produced by Du Pont Kabushiki Kaisha) was used instead of the fluorinated oil 1.

Example 3

A sliding elastic body was prepared in the same manner as in Example 1, except that a fluorinated oil 3 (Krytox GPL107 (kinematic viscosity (40° C.): 440 mm$^2$/s) produced by Du Pont Kabushiki Kaisha) was used instead of the fluorinated oil 1.

Example 4

A sliding elastic body was prepared in the same manner as in Example 1, except that a fluorinated oil 4 (DEMNUM S-65 (viscosity (40° C.): 65 mm$^2$/s) produced by DAIKIN INDUSTRIES, ltd.) was used instead of the fluorinated oil 1.

Example 5

A sliding elastic body was prepared in the same manner as in Example 1, except that a fluorinated oil 5 (DEMNUM S-200 (viscosity (40° C.): 200 mm$^2$/s) produced by DAIKIN INDUSTRIES, ltd.) was used instead of the fluorinated oil 1.

Comparative Example 1

A rubber vulcanizate (vulcanized at 180° C. for 10 minutes) prepared by crosslinking a chlorobutyl rubber by triazine was used.

The sliding elastic bodies prepared in the examples and the comparative example were evaluated by the methods mentioned below.

(Friction Resistance)

To determine the friction resistance on the surface of the sliding elastic bodies, the vulcanized rubber gaskets (sliding elastic bodies) prepared in the examples and the comparative example were each set in a COP resin barrel of a syringe and then pushed towards the end of the barrel (push rate: 30 mm/min) using a tensile tester while friction resistance was measured. The values of the examples are expressed as a friction resistance index using the equation below, with the friction resistance of Comparative Example 1 being set equal to 100. A lower index indicates a lower friction resistance. (Friction resistance index)=(Friction resistance of each example)/(Friction resistance of Comparative Example 1)×100

TABLE 1

|  | Example | | | | | Comparative Example |
|---|---|---|---|---|---|---|
|  | 1 | 2 | 3 | 4 | 5 | 1 |
| Friction resistance index | 3.4 | 2.5 | 2.4 | 2.7 | 2.6 | 100 |

The results demonstrate that the sliding elastic bodies of the examples exhibited significantly reduced friction resistances and had good sliding properties. They also had sealing properties equivalent to those of Comparative Example 1.

(Protein Adsorption Test)

The surface of the sliding elastic body prepared in Example 2 was brought into contact with 1 mg/ml of a bovine serum albumin solution at 37° C. for 3 hours to adsorb the albumin onto the surface. The adsorbed albumin was extracted in accordance with JIS T9010. The amount of extracted albumin was measured by the Lowry method, and then calculated per area of the adsorbed surface. The adsorbed amount was 0.00 μg/cm² or less and very little adsorption was observed. This demonstrates good resistance to protein adsorption.

Thus, in the case where the present invention is applied to a gasket for a syringe plunger, sufficient sealing properties are achieved while the friction of the plunger with the syringe barrel is reduced; therefore, operations using such a syringe can be easily and accurately performed. Moreover, very little protein is adsorbed on the surface, and excellent resistance to protein adsorption is also obtained.

Furthermore, the aforementioned effects can be expected when the present invention is applied to grooves formed on the tread of a tire for use on vehicles such as passenger cars, sidewalls thereof, diaphragms, the sliding surfaces of skis or snowboards, swimsuits, road signs, sign boards, or the like.

REFERENCE SIGNS LIST

1 Syringe gasket
12 Elastic body
13 Fluororesin film
14 Fluorinated oil
15 Liquid-contacting portion
16 Sliding portion (circular sealing portion)
17 Insert hole
2 Tread portion
3*a* Longitudinal center groove
3*b* Longitudinal shoulder groove
5 Fine groove
6 Beveled intermediate groove
7 Connecting groove
8, 8*a*, 8*b* Lateral shoulder groove

The invention claimed is:

1. A syringe gasket which comprises a sliding elastic body having a laminated surface that is fully or partially laminated with a fluororesin film, wherein the laminated surface is treated with a fluorinated oil, and the fluorinated oil comprises a compound represented by formula (2):

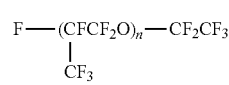

$$F-(CFCF_2O)_n-CF_2CF_3 \atop | \atop CF_3 \qquad (2)$$

wherein n represents an integer of 1 or more.

2. The syringe gasket according to claim 1, wherein the fluororesin film comprises polytetrafluoroethylene, modified polytetrafluoroethylene, a tetrafluoroethylene-ethylene copolymer, a tetrafluoroethylene-perfluoro(alkyl vinyl ether) copolymer, a tetrafluoroethylene-hexafluoropropylene copolymer, polyvinylidene fluoride, polychlorotrifluoroethylene, or a chlorotrifluoroethylene-ethylene copolymer.

3. The syringe gasket according to claim 1, wherein the fluorinated oil has a kinematic viscosity at 40° C. of 40 mm²/s or higher.

4. The syringe according to claim 2, wherein the fluorinated oil has a kinematic viscosity at 40° C. of 40 mm²/s or higher.

* * * * *